United States Patent
Dochnahl et al.

(10) Patent No.: US 8,362,272 B2
(45) Date of Patent: Jan. 29, 2013

(54) PROCESS FOR PREPARING 1,3-DISUBSTITUTED PYRAZOLE COMPOUNDS

(75) Inventors: Maximilian Dochnahl, Mannheim (DE); Michael Keil, Freinsheim (DE); Bernd Wolf, Fussgoenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/505,909

(22) PCT Filed: Oct. 28, 2010

(86) PCT No.: PCT/EP2010/066372
§ 371 (c)(1), (2), (4) Date: May 3, 2012

(87) PCT Pub. No.: WO2011/054732
PCT Pub. Date: May 12, 2011

(65) Prior Publication Data
US 2012/0220781 A1 Aug. 30, 2012

(30) Foreign Application Priority Data
Nov. 5, 2009 (EP) .................................... 09175079

(51) Int. Cl.
C07D 231/10 (2006.01)
(52) U.S. Cl. .................. 548/373.1; 548/374.1
(58) Field of Classification Search ............... 548/373.1, 548/374.1
See application file for complete search history.

(56) References Cited

U.S. PATENT DOCUMENTS

| 5,498,624 | A | 3/1996 | McLoughlin et al. |
| 6,706,911 | B1 | 3/2004 | Lui et al. |
| 2006/0252944 | A1 | 11/2006 | Lantzsch et al. |
| 2009/0326242 | A1 | 12/2009 | Pazenok et al. |

FOREIGN PATENT DOCUMENTS

| WO | WO 03/051820 | 6/2003 | |
| WO | WO 2005/042468 | * 5/2005 | ............... 548/365.1 |
| WO | WO 2008/022777 | 2/2008 | |
| WO | WO 2011/054733 | 5/2011 | |

OTHER PUBLICATIONS

Agafonov, N.E., et al., "Novel route to N-Alkyl- and N,N-dialkylhydrazines by high-pressure alkylation of azines", Russian Chemical Bulletin, International Edition, Mar. 2004, p. 714-716, vol. 53, No. 3.
Attanasi, Orazio, et al., "Flexible Protocol for the Chemo-and Regioselective Building of Pyrroles and Pyrazoles by Reactions of Danishefsky's Dienes with 1,2-D/iaza-1,3-butadienes", Organic Letters, 2008, p. 1983-1986, vol. 10, No. 10.
Eisch, John J., et al. "Vanadium(I) Chloride and Lithium Vanadium(I) Dihydride as Selective Epimetallating Reagents for π- and σ-Bonded Organic Substrates", Eur. J. Org. Chem., 2008, p. 4482-4492.
Harries, C., et al., "Ueber Die Methylirung des Hydrazinhydrats", Chemische Berichte, 1898, p. 56-64, vol. 31, No. 1.
International Search Report completed Nov. 22, 2010, in International Application No. PCT/EP2010/066372, filed Oct. 28, 2010.
International Preliminary Report on Patentability dated Sep. 21, 2011, from corresponding International Application No. PCT/EP2010/066372, filed Oct. 28, 2010.
Mathur, S.S., et al., "Preparation and Reactions of Quaternary Aldazines", Tetrahedron Letters, 1975, p. 785-788, No. 10.
Posvic, Harvey, et al. "Variations of the Fischer and Piloty Syntheses", J. Org. Chem., 1974, p. 2575-2580, vol. 39, No. 17.
Thiele, Johannes, "Ueber Nitrosohydrazine, Isozotate and Azoverbindungen der Fettreihe", Justus Liebigs Annalen der Chemie, 1910, p. 239-268.

* cited by examiner

*Primary Examiner* — Rebecca Anderson
*Assistant Examiner* — Samantha Shterengarts
(74) *Attorney, Agent, or Firm* — Brinks Hofer Gilson & Lione

(57) ABSTRACT

A process for preparing 1,3-disubstituted pyrazole compounds.

19 Claims, No Drawings

PROCESS FOR PREPARING 1,3-DISUBSTITUTED PYRAZOLE COMPOUNDS

This application is a National Stage application of International Application No. PCT/EP2010/066372, filed Oct. 28, 2010, the entire contents of which is hereby incorporated herein by reference. This application also claims priority under 35 U.S.C. §119 to European Patent Application No. 09175079.4, filed Nov. 5, 2009, the entire contents of which is hereby incorporated herein by reference.

The present invention relates to a process for preparing compounds of the formula I

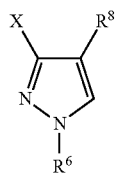

(I)

in which
X is hydrogen, branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein
 aryl or hetaryl are unsubstituted or optionally comprising one or more substituents independently of one another selected from the group consisting of $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl and aryl, carbonitrile and carboxylic ester; or
 a $CX^1X^2X^3$ group, in which
  $X^1$, $X^2$ and $X^3$ are each independently hydrogen, fluorine or chlorine, where $X^1$ may also be $C_1$-$C_8$-alkyl or $C_1$-$C_4$-haloalkyl; or
$R^6$ is branched or unbranched $C_2$-$C_8$-alkenyl or $C_3$-$C_8$-akynyl; $C_3$-$C_8$-cycloalkyl, aryl or hetaryl, wherein
 aryl or hetaryl are unsubstituted or optionally comprising one or more substituents independently of one another selected from the group consisting of halogen, hydroxo, amino, mercapto, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;
$R^8$ is hydrogen, methyl, hydroxymethylene, halogen, CHO, CN, $NO_2$ or a $CO_2R^{8a}$ group, in which
 $R^{8a}$ is $C_5$-$C_6$-cycloalkyl, optionally substituted phenyl or $C_1$-$C_6$-alkyl, which may optionally be substituted by $C_1$-$C_4$-alkoxy, phenyl or $C_3$-$C_6$-cycloalkyl.

Pyrazoles of the formula I are important starting materials for a number of active pharmaceutical ingredients and crop protection active ingredients, especially for 1,3-disubstituted pyrazol-4-ylcarboxanilides, as described, for example, in U.S. Pat. No. 5,498,624, EP 545099 A1, EP 589301 A1, WO 92/12970, WO 03/066610, WO 2006/024389, WO 2007/003603, WO 2007/006806.

1,3-Disubstituted pyrazole compounds of the formula I are prepared typically by cyclizing suitable 1,3-difunctional compounds with substituted hydrazine compounds, or by reacting 1,3-difunctional compounds with hydrazine, followed by an alkylation to introduce the substituent on the nitrogen (1 position). A fundamental disadvantage in this procedure is the lack of regioselectivity of the cyclization of 1,3-difunctional compounds with substituted hydrazine compounds, and also the lack of regioselectivity of the N-alkylation of pyrazoles, such that, in both cases, not only the desired pyrazole compound but also the 1,5-substituted is formed.

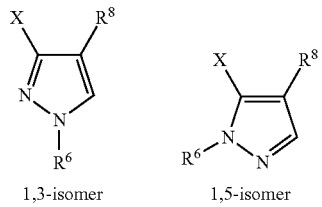

1,3-isomer     1,5-isomer

Regardless of the fact that the lack of selectivity leads to yield losses, 1,3-isomer of the formula I and 1,5-isomer of the formula I' can frequently be separated only with difficulty. In order to achieve acceptable selectivities, the reactions therefore have to be carried out at low temperatures, which considerably increases the apparatus complexity. In addition, the regioselectivity is also not entirely satisfactory under cold conditions.

U.S. Pat. No. 5,498,624, inter alis, describe a process for preparing (3-difluoromethyl-1-methyl-pyrazol-4-yl)carboxylic esters, in which α-ethoxymethylene-4,4-difluoro-3-oxobutyric ester is cyclized with methylhydrazine to give the pyrazole compound. WO 92/12970 discloses a comparable process in which 4,4-difluoro-3-oxobutyric ester is reacted gradually with triethyl orthoformiate and with methylhydrazine, which forms ethoxymethylene-4,4-difluoro-3-oxobutyric ester as an intermediate. The selectivity for the desired isomer is not satisfactory.

WO 2003/051820 and WO 2005/042468 describe the cyclization of 2-haloacyl-3-aminoacrylic esters with alkylhydrazines to give 1-alkyl-3-haloalkylpyrazole-4-carboxylic esters. The selectivity for the desired isomer is not satisfactory.

WO 2008/022777 describes a process for preparing 1-substituted 3-(dihalomethyl)pyrazole-4-carboxylic esters, in which vinylogous amidinium salts, which are obtainable by reacting α-(halomethyl)difluoromethylamines with acrylates in the presence of a Lewis acid, are reacted with substituted hydrazines. The selectivity for the desired isomer is not satisfactory.

It is therefore an object of the invention to provide a process for preparing 1,3-disubstituted pyrazole compounds of the formula I cited at the outset, which affords the desired 1,3-isomer of the formula I with high yields and good selectivity.

It has been found that, surprisingly, 1,3-disubstituted pyrazole compounds of the formula I defined at the outset can be prepared in a simple manner with high yields and high regioselectivity for the desired 1,3-isomer when suitable aminal compounds of the formula II described below are reacted with a compound of the formula III described below.

Accordingly, the present invention relates to a process for preparing 1,3-disubstituted pyrazole compounds of the formula I defined at the outset, which comprises the following steps:
(i) reacting a compound of the formula II with a compound of the formula III

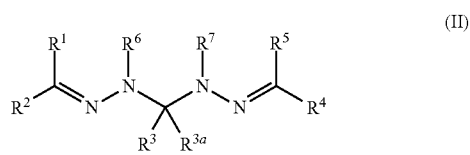

(II)

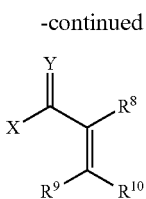
(III)

in which

X, $R^6$ and $R^8$ are each as defined for formula I;

$R^1$, $R^2$, $R^3$, $R^{3a}$, $R^4$, $R^5$ and $R^7$ are each independently hydrogen, branched or unbranched $C_2$-$C_8$-alkenyl or $C_3$-$C_8$-akynyl; $C_3$-$C_8$-cycloalkyl, aryl or hetaryl, wherein aryl or hetaryl are unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;

Y is oxygen, an $NR^{y1}$ group or an $[NR^{y2}R^{y3}]^+Z^-$ group, in which $R^{y1}$, $R^{y2}$ and $R^{y3}$ are each independently $C_1$-$C_8$-alkyl, $C_3$-$C_8$-cycloalkyl, optionally substituted phenyl or optionally substituted phenyl-$C_1$-$C_4$-alkyl, or $R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and $Z^-$ is an anion.

$R^9$ is halogen, $OR^{9a}$, $SR^{9a}$ or an $NR^{9b}R^{9b}$ group, in which $R^{9a}$, $R^{9b}$ and $R^{9c}$ are each independently $C_1$-$C_8$-alkyl, $C_3$-$C_8$-cycloalkyl, optionally substituted phenyl or optionally substituted phenyl-$C_1$-$C_4$-alkyl, or $R^{9b}$ and $R^{9b}$ together with the nitrogen atom to which they are bonded are an N-bonded 5- to 8-membered, saturated, optionally substituted heterocycle which, as well as the nitrogen atom, may also comprise 1 or 2 further heteroatoms selected from N, O and S as ring atoms; or a $CX^1X^2X^3$ group, in which $X^1$, $X^2$ and $X^3$ are each independently hydrogen, fluorine or chlorine, where $X^1$ may also be $C_1$-$C_8$-alkyl or $C_1$-$C_4$-haloalkyl;

$R^{10}$ is hydrogen, halogen or $C_1$-$C_8$-alkyl;

(ii) treating the reaction product obtained with an acid, optionally in the presence of water.

The process according to the invention is very advantageously, since the desired 1,3-disubstituted pyrazoles is prepared with a high yield and high regioselectivity based on the desired 1,3-isomer of the formula I.

The terms used for organic groups in the definition of the variables are, for example the expression "halogen", collective terms which represent the individual members of these groups of organic units.

The prefix $C_x$-$C_y$ denotes the number of possible carbon atoms in the particular case.

halogen: fluorine, bromine, chlorine or iodine, especially fluorine, chlorine or bromine;

alkyl and the alkyl moieties of composite groups such as, for example, alkoxy, alkylamino, alkoxycarbonyl: saturated straight-chain or branched hydrocarbon radicals having 1 to 4, 6 or 8 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 2, 4, 6 or 8 carbon atoms (as mentioned above), where some or all of the hydrogen atoms in these groups are replaced by halogen atoms as mentioned above. In one embodiment, the alkyl groups are substituted at least once or completely by a particular halogen atom, preferably fluorine, chlorine or bromine. In a further embodiment, the alkyl groups are partially or fully halogenated by different halogen atoms; in the case of mixed halogen substitutions, the combination of chlorine and fluorine is preferred. Particular preference is given to ($C_1$-$C_3$)-haloalkyl, more preferably ($C_1$-$C_2$)-haloalkyl, such as chloromethyl, bromomethyl, dichloromethyl, trichloromethyl, fluoromethyl, difluoro-methyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl and also the alkenyl moieties in composite groups, such as alkenyloxy: unsaturated straight-chain or branched hydrocarbon radicals having 2 to 4, 2 to 6 or 2 to 8 carbon atoms and one double bond in any position. According to the invention, it may be preferred to use small alkenyl groups, such as ($C_2$-$C_4$)-alkenyl; on the other hand, it may also be preferred to employ larger alkenyl groups, such as ($C_5$-$C_8$)-alkenyl. Examples of alkenyl groups are, for example, $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl and the alkynyl moieties in composite groups: straight-chain or branched hydrocarbon groups having 2 to 4, 2 to 6 or 2 to 8 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl and also the cycloalkyl moieties in composite groups: mono- or bicyclic saturated hydrocarbon groups having 3 to 8, in particular 3 to 6, carbon ring members, for example $C_3$-$C_6$-cycloalkyl, such as cyclopropyl, cyclobutyl, cyclopentyl, cyclohexyl, cycloheptyl or cyclooctyl. Examples of bicyclic radicals comprise bicyclo[2.2.1]heptyl, bicyclo[3.1.1]heptyl, bicyclo[2.2.2]octyl and bicyclo[3.2.1]octyl. In this connection, optionally substituted $C_3$-$C_8$-cycloalkyl means a cycloalkyl radical having from 3 to 8 carbon atoms, in which at least one hydrogen atom, for example 1, 2, 3, 4 or 5 hydrogen atoms, is/are replaced by substituents which are inert under the conditions of the reaction. Examples of inert substituents are CN, $C_1$-$C_6$-alkyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl;

alkoxy: an alkyl group as defined above which is attached via an oxygen, preferably having 1 to 8, more preferably 2 to 6, carbon atoms. Examples are: methoxy, ethoxy, n-propoxy, 1-methylethoxy, butoxy, 1-methylpropoxy, 2-methylpropoxy or 1,1-dimethylethoxy, and also for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

haloalkoxy: alkoxy as defined above, where some or all of the hydrogen atoms in these groups are replaced by halogen atoms as described above under haloalkyl, in particular by fluorine, chlorine or bromine. Examples are $OCH_2F$, $OCHF_2$, $OCF_3$, $OCH_2Cl$, $OCHCl_2$, $OCCl_3$, chlorofluoromethoxy, dichlorofluoromethoxy, chlorodifluoro-methoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy; and also 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

6- to 10-membered aryl: aromatic cyclus with 6, 7, 8, 9 oder 10 C atoms. Examples of preferred aryl are phenyl or naphthyl;

optionally substituted phenyl: unsubstituted phenyl or describes phenyl which bears 1, 2, 3, 4 or 5 and especially 1, 2 or 3 substituents which are inert under the conditions of the reaction. Examples of inert substituents are halogen, especially fluorine, chlorine or bromine, CN, $NO_2$, $C_1$-$C_6$-alkyl, $C_1$-$C_6$-alkylthio, $C_1$-$C_6$-alkylsulfonyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl;

optionally substituted phenyl-$C_1$-$C_6$-alkyl: $C_1$-$C_6$-alkyl in which one of the hydrogen atoms is replaced by an optionally substituted phenyl group. Examples are benzyl, 4-methylbenzyl, phenylethyl etc.;

a 5-, 6-, 7-, 8-membered saturated or partially unsaturated heterocycle which contains 1, 2, 3 or 4 heteroatoms from the group consisting of O, N and S, where the heterocycle in question may be attached via a carbon atom or, if present, via a nitrogen atom. In particular:

a five- or six-membered saturated or partially unsaturated heterocycle which comprises one, two, three or four heteroatoms from the group consisting of O, N and S as ring members: for example monocyclic saturated or partially unsaturated heterocycles which, in addition to carbon ring members, comprise one, two or three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydro-oxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexa-hydropyridazinyl, 2-hexahydropyrimidinyl, 4-hexahydropyrimidinyl, 5-hexahydro-pyrimidinyl, 2-piperazinyl, 1,3,5-hexahydrotriazin-2-yl and 1,2,4-hexahydrotriazin-3-yl and also the corresponding-ylidene radicals;

a seven-membered saturated or partially unsaturated heterocycle which comprises one, two, three or four heteroatoms from the group consisting of O, N and S as ring members: for example mono- and bicyclic heterocycles having 7 ring members which, in addition to carbon ring members, comprise one, two or three nitrogen atoms and/or one oxygen or sulfur atom or one or two oxygen and/or sulfur atoms, for example tetra- and hexahydroazepinyl, such as 2,3,4,5-tetrahydro[1H]azepin-1-, -2-, -3-, -4-, -5-, -6- or -7-yl, 3,4,5,6-tetra-hydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, hexahydroazepin-1-, -2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydroazepin-1-, -2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding ylidene radicals;

optionally substituted heterocycle: a saturated heterocycle which is bonded via a ring nitrogen atom and has 5, 6, 7 or 8 ring atoms, where, as well as the nitrogen atom, the ring atoms also further which is unsubstituted or bears 1, 2, 3, 4 or 5 and especially 1, 2 or 3 substituents which are inert under the conditions of the reaction. Examples of inert substituents are CN, $C_1$-$C_6$-alkyl, $C_1$-$C_6$-alkylsulfonyl, $C_1$-$C_6$-alkoxy, $C_3$-$C_6$-cycloalkyl, and $C_1$-$C_4$-alkoxy-$C_1$-$C_6$-alkyl. The heterocycle may, as well as the nitrogen atom in position 1 and the ring carbon atoms, also comprise 1 or 2 further heteroatoms selected from N, O and S as ring atoms. Examples of N-bonded, 5- to 8-membered, saturated, optionally substituted heterocycles are pyrrolidin-1-yl, piperidin-1-yl, morpholin-4-yl, piperazin-1-yl and N-methylpiperazin-1-yl;

alkylthio: alkyl as defined above which is attached via an S atom;

amino: $NR^1R^2$ group, in which $R^1$ and $R^2$ can be alkyl, aryl or heteroaryl as defined above, which is attached via an N atom alkylamino: alkyl as defined above which is attached via N atom;

haloalkylthio: haloalkyl as defined above which is attached via an S atom;

hydroxo: OH group which is attached via an O atom;

carbonitrile: CN group which is attached via an C atom;

aldehyde: CHO group, which is attached via an C atom;

carboxylic ester: $COOR^1$ group, in which $R^1$ can be alkyl, aryl or heteroaryl as defined above, which is attached via an C atom;

mercapto: SH group which is attached via an S atom.

The process according to the invention is suitable especially for preparing compounds of the formula I, in which X is a $CX^1X^2X^3$ group in which $X^1$, $X^2$ and $X^3$ are each as defined above. More particularly, at least one of the $X^1$ and $X^2$ radicals is different than hydrogen. More particularly, $X^1$ and $X^2$ are each fluorine. $X^3$ is preferably hydrogen, fluorine or chlorine. Examples of preferred $CX^1X^2X^3$ radicals are dichloromethyl, chlorofluoromethyl, difluoromethyl, chlorodifluoromethyl and trifluoromethyl. In a specific embodiment, X is a $CHF_2$ group.

Furthermore, the process according to the invention is suitable especially for preparing compounds of the formula I, in which $R^6$ is $C_1$-$C_8$-alkyl, particularly $C_1$-$C_6$-alkyl. More particularly, the process according to the invention is suitable especially for preparing compounds of the formula I, in which $R^6$ is $C_1$-$C_3$-alkyl. Examples of preferred substituents are methyl, ethyl, propyl. In a specific embodiment, $R^6$ is methyl.

A preferred embodiment of the invention relates to the preparation of pyrazole compounds of the formula I in which $R^8$ is a CN group or especially $COOR^{8a}$ in which $R^{8a}$ is as defined above and is in particular $C_1$-$C_6$-alkyl and especially $C_1$-$C_4$-alkyl.

Another embodiment of the invention relates to the preparation of pyrazole compounds of the formula I in which $R^8$ is hydrogen.

The pyrazole compounds of the formula I as defined above are prepared by using a compound of the formula II and a compound of the formula III.

The pyrazole compounds of the formula I as defined above are preferably prepared by using a compound of the formula II, in which $R^1$, $R^2$, $R^3$, $R^{3a}$, $R^4$ and $R^5$ are each independently aryl, which is unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkoxy, $C_1$-$C_4$-haloalkylthio, $C_3$-$C_8$-cycloalkyl, alkenyl, aryl, carbonitrile, carboxylic ester or aldehyde. More particularly, the pyrazole compounds of the formula I as defined above are prepared by using a compound of the formula II, in which $R^1$, $R^3$ and $R^4$ are each aryl, which is unsubstituted or optionally comprising one or more substituents as defined above, and $R^2$, $R^{3a}$ and $R^5$ are each hydrogen. Examples of preferred aryl substituents are phenyl, 4-methoxyphenyl, 2-furyl and 2-thienyl. In a specific embodiment, $R^1$, $R^3$ and $R^4$ are each phenyl and $R^2$, $R^{3a}$ and $R^5$ are each hydrogen.

The pyrazole compounds of the formula I as defined above are preferably prepared by using a compound of the formula II, in which $R^6$ and $R^7$ are each $C_1$-$C_8$-alkyl, particularly $C_1$-$C_6$-alkyl. More particularly, the pyrazole compounds of the formula I as defined above are preferably prepared by using a compound of the formula II, in which $R^6$ and $R^7$ are each $C_1$-$C_3$-alkyl. Examples of preferred substituents are methyl, ethyl, propyl. In a specific embodiment, $R^6$ and $R^7$ are each methyl.

In a first embodiment of the invention, the pyrazole compounds of the formula I are prepared by using a compound of the formula III in which Y is oxygen and $R^{10}$ is hydrogen. Such compounds are also referred to hereinafter as compounds IIIa. Compounds of the formula IIIa in which $R^8$ is a $COOR^{8a}$ group in which $R^{8a}$ is as defined above and is especially $C_1$-$C_6$-alkyl and especially $C_1$-$C_4$-alkyl are also referred to hereinafter as compounds IIIa.1. Compounds of the formula IIIa in which $R^8$ is hydrogen are also referred to hereinafter as compounds IIIa.2.

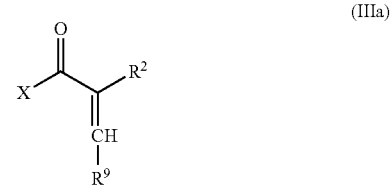

(IIIa)

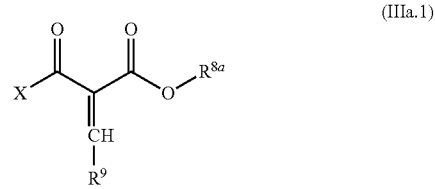

(IIIa.1)

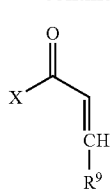
(IIIa.2)

In the formulae IIIa, IIIa.1 and IIIa.2, $R^9$ and X are each as defined above.

More particularly, X in the formulae IIIa, IIIa.1 and IIIa.2 is a $CX^1X^2X^3$ group in which $X^1$, $X^2$ and $X^3$ are each as defined above. In particular, at least one of the $X^1$ and $X^2$ radicals is different than hydrogen. More particularly, $X^1$ and $X^2$ are each fluorine. $X^3$ is preferably hydrogen, fluorine or chlorine. Examples of particularly preferred $CX^1X^2X^3$ groups are dichloromethyl, trifluoromethyl, chlorodifluoromethyl, fluorochloromethyl and difluoromethyl. In a specific embodiment, X is a $CHF_2$ group.

In a second embodiment of the invention, the pyrazole compounds of the formula I are prepared by using a compound of the formula III in which Y is an $[NR^{y2}R^{y3}]^+Z$ group and $R^{10}$ is hydrogen. Such compounds are also referred to hereinafter as compounds IIIb. Compounds of the formula IIIb in which $R^8$ is a $COOR^{8a}$ group in which $R^{8a}$ is as defined above and is in particular $C_1$-$C_6$-alkyl are also referred to hereinafter as compounds IIIb.1. Compounds of the formula IIIa in which $R^8$ is hydrogen are also referred to hereinafter as compounds IIIb.2.

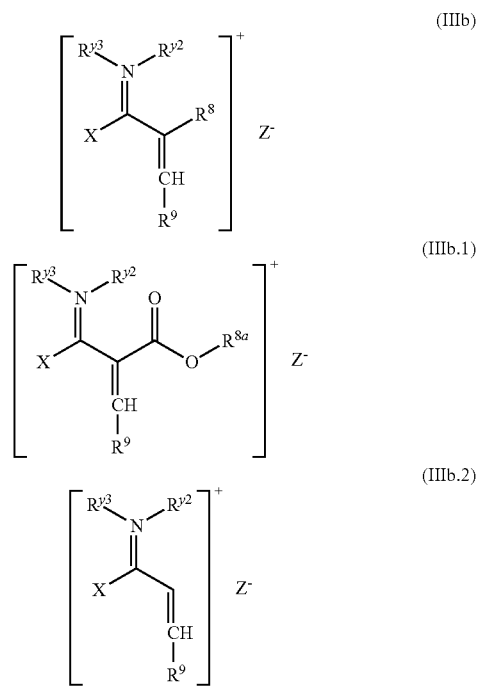

In the formulae IIIb, IIIb.1 and IIIb.2, $R^{y2}$, $R^{y3}$, Z, $R^9$ and X are each as defined above.

More particularly, X in the formulae IIIb, IIIb.1 and IIIb.2 is a $CX^1X^2X^3$ group in which $X^1$, $X^2$ and $X^3$ are each as defined above. More particularly, at least one of the $X^1$ and $X^2$ radicals is different than hydrogen. More particularly, $X^1$ and $X^2$ are each fluorine. $X^3$ is preferably hydrogen, fluorine or chlorine. Examples of particularly preferred $CX^1X^2X^3$ groups are trifluoromethyl, chlorodifluoromethyl, fluorochloromethyl and difluoromethyl. More particularly, the $CX^1X^2X^3$ group in the formulae IIIb, IIIb.1 and IIIb.2 is CHClF or $CHF_2$.

$R^{y2}$ and $R^{y3}$ are in particular $C_1$-$C_4$-alkyl and especially methyl.

$Z^-$ is an anion or an anion equivalent, which is preferably derived from a Lewis acid such as MgF2, $BF_3$, $BCl_3$, $AlCl_3$, $AlF_3$, $ZnCl_2$, $PF_5$, $SbF_5$, $BiCl_3$, $GaCl_3$, $SnCl_4$, or $SiCl_4$, for example is fluoride, $[MgF_3]^-$, $[BF_4]^-$, $[BCl_3F]^-$, $[AlF_4]^-$, $[AlCl_3F]^-$, $[ZnCl_2F]^-$, $[PF_6]^-$, $[SbF_6]^-$, $[BiCl_3F]^-$, $[GaCl_3F]^-$, $[SnCl_4F]^-$ or $[SiCl_4F]^-$.

In a first variant of the process according to the invention, $R^9$ in the formulae III, IIIa, IIIa.1 and IIIa.2, IIIb, IIIb.1 and IIIb.2 is an $OR^{9a}$ group. In this case, $R^{9a}$ is as defined above and is in particular $C_1$-$C_4$-alkyl and especially methyl or ethyl.

In a second variant of the process according to the invention, $R^9$ in the formulae III, IIIa, IIIa.1 and IIIa.2, IIIb, IIIb.1 and IIIb.2 is an $NR^{9b}R^{9c}$ group. In this group, $R^{9b}$ and $R^{9c}$ are each as defined above and are in particular $C_1$-$C_4$-alkyl and especially methyl or ethyl, or $R^{9b}$ and $R^{9c}$ together with the nitrogen atom to which they are bonded are an N-bonded 5- to 8-membered, saturated heterocycle which, as well as the nitrogen atom, may also have 1 or 2 further heteroatoms selected from N, O and S as ring atoms and which may optionally bear 1 or 2 $C_1$-$C_4$-alkyl groups. Examples of the latter cyclic $NR^{9b}R^{9c}$ groups are pyrrolidin-1-yl, morpholin-4-yl, piperidin-1-yl and 4-methylpiperazin-1-yl.

In the step (i) of the process according to the present invention the compound of the formula II is reacted with the compound of the formula III typically at temperatures in the range from −20 to 180° C., especially in the range from 20 to 100° C.

For the reaction, the compounds II and III are preferably used in a ratio corresponding to the stoichiometry of the reaction, but it is also possible to deviate from the stoichiometry. Typically, the molar ratio of compound I to compound III is in the range from 5:1 to 1:5, frequently in the range from 3:1 to 1:3 and especially in the range from 2:1 to 1:2.

Typically, the reaction in step (i) is effected in an inert organic solvent. Examples of inert organic solvents are especially aprotic organic solvents such as aromatic hydrocarbons and halohydrocarbons, for example benzene, toluene, xylenes, cumene, chlorobenzene and tert-butylbenzene, cyclic or acyclic ethers such as diethyl ether, diisopropyl ether, tert-butyl methyl ether (MTBE), tert-butyl ethyl ether, tetrahydrofuran (THF) or dioxane, nitriles such as acetonitrile and propionitrile, aliphatic halohydrocarbons such as dichloromethane, dichloroethane, trichloromethane and mixtures thereof.

For the reaction of the compounds of the formula II with the compound of the formula III, the procedure will generally be to combine the compound of the formula II, preferably in the form of a solution in one of the aforementioned inert organic solvents, with the compound of the formula III, which is preferably likewise used in the form of a solution in one of the aforementioned inert organic solvents. In this case, the compound of the formula II can be initially charged as a solution in an organic solvent and the compound II can be added, preferably as a solution. Alternatively, the compound III can be initially charged as a solution in an organic solvent and the compound of the formula I can be added, preferably as a solution. The compound of the formula II and the compound of the formula III can be combined in the abovementioned temperature ranges. The procedure will frequently be that the compounds II and III are combined at temperatures in the range from 20 to 80° C. The reaction time is typically in the range from 0.5 h to 15 h.

In the step (ii) the reaction is effected in the presence of an acid, especially of a Broensted acid. Preferred acids have a pKa of not more than 4, especially not more than 3 or not more than 2 in dilute (e.g. 0.01 M) aqueous solution at 25° C. Preferred acids are hydrohalic acids such as HF, HCl and HBr, especially in the form of their aqueous solutions, sulfuric acid, phosphoric acid, $HBF_4$, and organic sulfonic acids, for example aromatic sulfonic acids of the formula $Ar—SO_3H$ in which Ar is optionally substituted phenyl, such as benzylsulfonic acid and p-toluenesulfonic acid, and also aliphatic sulfonic acids such as methanesulfonic acid, ethanesulfonic acid and trifluoromethanesulfonic acid. Likewise suitable are aliphatic and aromatic carboxylic acids such as formic acid, chloroacetic acid, dichloroacetic acid, trichloroacetic acid, trifluoroacetic acid, salicylic acid and 2-chlorobenzoic acid. It will be appreciated that mixtures of the aforementioned acids are also suitable.

For the reaction in step (ii), catalytic amounts of acid are generally sufficient. The acid can, however, also be used in a stoichiometric or superstoichiometric amount. In general, the acid is used in an amount of from 0.01 to 10 mol and especially in the amount of from 0.02 to 5 mol per mol of compound II, or, in the case of in situ preparation of the compound II, in an amount of from 0.01 to 10 mol and especially in an amount of from 0.02 to 2 mol per mol of compound II.

Typically, the reaction in step (ii) is effected in the presence of an organic solvent or solvent mixture. Suitable organic solvents for the reaction in step (ii) are protic polar solvents, for example aliphatic alcohols having preferably from 1 to 4 carbon atoms, such as methanol, ethanol, n-propanol, isopropanol, n-butanol, isobutanol or tert-butanol, or carboxylic acids such as acetic acid, or aromatic polar solvents such as aromatic hydrocarbons such as benzene, toluene, xylenes, cumene, chlorobenzene, nitrobenzene or tert-butylbenzene, aprotic polar solvents, for example cyclic or acyclic ethers such as diethyl ether, diisopropyl ether, tert-butyl methyl ether (MTBE), tert-butyl ethyl ether, tetrahydrofuran (THF) or dioxane, cyclic or acyclic amides such as dimethylformamide, dimethylacetamide, N-methylpyrrolidone or tetramethylurea, or aliphatic nitriles such as acetonitrile or propionitrile, and mixtures of the aforementioned solvents.

The reaction in step (ii) of the process according to the invention is effected typically at temperatures in the range from 0 to 150° C., especially in the range from 10 to 80° C. The reaction time is typically in the range from 0.1 to 15 h.

In step (ii), the desired 1,3-disubstituted pyrazole compound I is obtained in high yield.

The desired pyrazole compound I can be isolated from the reaction mixture by customary methods, by means of precipitation, crystallization or distillation, or be processed further to conversion products in the form of the reaction mixture or alternatively it can be used to a further synthesis step without purification.

The compounds of the formula II and III used in the process according to the invention are known, for example, from the prior art cited at the outset or can be prepared in analogy to the methods described there.

The aminal compounds of the formula II are prepared typically by reacting a mono-alkylhydrazine, in particular, mono-methylhydrazine, with an aldehyde as described, for example, in Chem. Ber., 1898, pages 56 to 64.

Compounds of the formula III in which Y is oxygen and $R^8$ is an $OR^{8a}$ group are known, for example, from U.S. Pat. No. 5,498,624, JACS, 73, 3684, WO 92/12970, Chem. Ber. 1982, 115, 2766, Journal of Medicinal Chemistry, 2000, Vol. 43, No. 21 and the prior applications WO 2008/053043 and EP 07109463.5, or can be prepared in analogy to the processes described there, for example by reacting alkyl vinyl ethers of the formula VI ($R^8$=H) or acrylic compounds of the formula VI ($R^8$=CN or $CO_2R^{8a}$) with acyl halides (Q=halogen) or acyl anhydrides (Q=OC(O)X) of the formula VII according to the following scheme 1, or by reacting β-keto esters of the formula VIII ($R^8$=$CO_2R^{8a}$) or β-keto nitriles VIII ($R^8$=CN) with orthoformic esters of the formula IX according to the following scheme 2.

Scheme 1

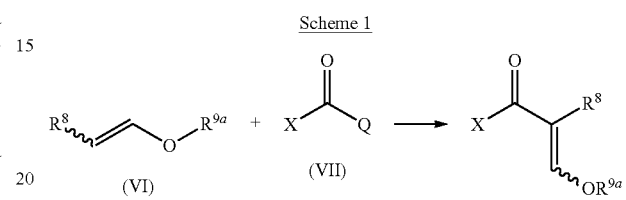

Scheme 2

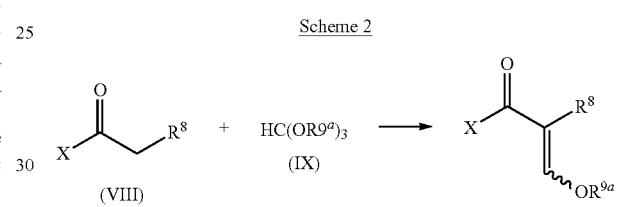

In schemes 1 and 2, the variables $R^8$, $R^{9a}$ and X are each as defined above. Q is especially fluorine, chlorine or an OC(O)X radical in which X has one of the definitions given above.

Compounds of the formula III in which Y is oxygen and $R^9$ is an $NR^{9b}R^{9c}$ group are known, for example, from WO 03/051820, WO 2005/042468 and the prior applications WO 2008/077907, EP 08155612.8 and EP 08155611.0 or can be prepared in analogy to the processes described there. For example, compounds of the formula III where $R^8$=H and $R^9$=$NR^{9b}R^{9c}$ can be prepared by reacting the alkali metal salts of β-formyl ketones of the formula X C(O)—$CH_2$—CHO, especially from their sodium salts, by reacting with hydrochlorides of secondary amines $HNR^{9b}R^{9c}$. Compounds of the formula III where $R^8$=CN or $CO_2R^{8a}$ can be prepared, for example, by reacting corresponding 3-aminoacrylic compounds X with the acyl compounds of the formula VII described in scheme 1 by the reaction shown in scheme 3.

Scheme 3

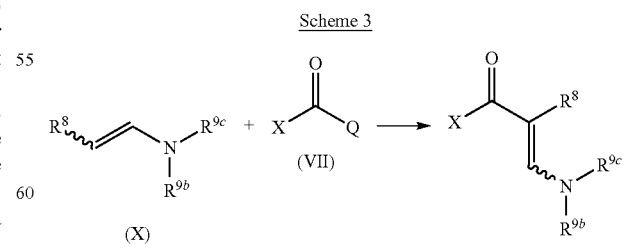

Compounds of the formula III in which Y is an $[NR^{y1}R^{y2}]$ $Z^−$ group (compounds IIIb) can be prepared, for example, by the processes described in WO 2008/022777 and the prior application EP 07110397. According to these, III in which Y is an $[NR^{y1}R^{y2}]Z^-$ group are prepared typically by reacting α,α-difluoroamines of the formula XI with an olefinic compound of the formula XII in the presence of a Lewis acid such as $MgF_2$, $BF_3$, $BCl_3$, $AlCl_3$, $AlF_3$, $ZnCl_2$, $PF_5$, $SbF_5$, $BiCl_3$, $GaCl_3$, $SnCl_4$, or $SiCl_4$ by the process shown in scheme 4.

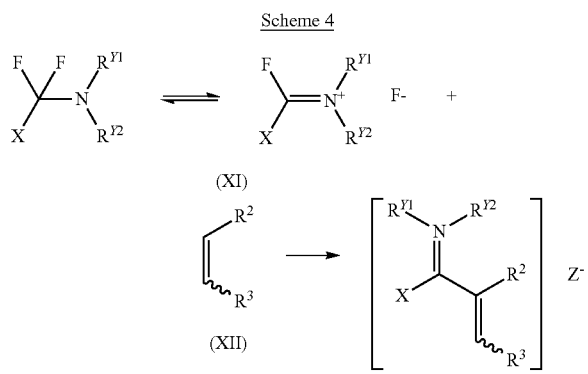

The pyrazole compounds of the formula I are valuable intermediates in the preparation of a compound of the formula Ia

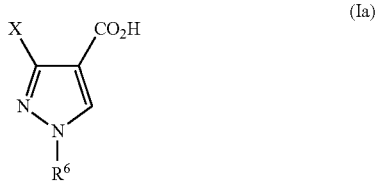

in which X and $R^6$ are each as defined for the formula I, comprising the following steps
a) providing a pyrazole compound of the formula I by a process according the process described here,
b) converting the compound I to a 1,3-disubstituted pyrazolecarboxylic acid of the formula Ia.

When the $R^8$ radical is a $CO_2R^{8a}$ or CN group, the conversion is effected typically by hydrolysis. Accordingly, a preferred embodiment of the invention relates to a process comprising the following steps:
a) the provision of a compound of the formula I by the process according to the invention as described and
b) hydrolysis of the compound I to form a 1,3-disubstituted pyrazolecarboxylic acid of the formula Ia.

The hydrolysis can be carried out under acid catalysis or by basic means or otherwise. The compound I can be used as such, i.e. after isolation. However, it is also possible to use the reaction mixture obtained in step a) for the hydrolysis without further purification, if appropriate after removal of volatile constituents such as solvents.

For the basic hydrolysis of the compound I, the compound of the formula I will typically be treated with an alkali metal hydroxide such as sodium hydroxide, potassium hydroxide or lithium hydroxide, preferably with an aqueous alkali metal hydroxide solution, especially an aqueous NaOH solution or an aqueous KOH solution, until complete hydrolysis of the ester, preferably while heating.

In the basic hydrolysis, the molar ratio of compound of the formula I to base is typically in the range from 10:1 to 1:10 and is especially approximately equimolar i.e. is in the range from 1.5:1 to 1:1.5, but a relatively large excess of base, for example up to 5 mol per mol of compound I, may also be advantageous.

Typically, the basic hydrolysis is effected in a diluent or solvent. Suitable diluents or solvents are, as well as water, also organic solvents which are stable toward alkali, and mixtures thereof with water. Examples of alkali-stable organic solvents are especially the aforementioned $C_1$-$C_4$-alkanols and the aforementioned acyclic ethers and the cyclic ethers. Preference is given to performing the hydrolysis in the aqueous phase, i.e. in water or a mixture of water with one of the aforementioned organic solvents, in which case the content of organic solvent in the aqueous phase typically does not exceed generally 30% by volume, based on the total amount of water and organic solvent.

Preference is given to performing the basic hydrolysis at temperatures of from 20 to 100° C. In general, the upper temperature limit is the boiling point of the solvent used when the reaction is conducted at ambient pressure. A reaction temperature of 100° C. and especially 90° C. will preferably not be exceeded. The reaction time depends here on the reaction temperature, the concentration and the stability of the particular ester bond. In general, the reaction conditions are selected such that the reaction time is in the range from 1 to 12 h, especially in the range from 2 to 8 h.

In a particularly preferred embodiment of the invention, for the preparation of a compound of the formula Ia, the pyrazole compound I obtained in step a), in the case that $R^8$ is $CO_2R^{8a}$ or CN, without intermediate isolation, advantageously together with the organic solvent, will be reacted with the aqueous alkali metal hydroxide solution. The alkali metal salt of the pyrazolecarboxylic acid Ia formed is obtained as an aqueous phase in addition to the organic phase, which can be removed by phase separation. Recycling of the organic solvent used can also be undertaken. The aqueous phase obtained in the phase separation comprises the alkali metal salt of the 1,3-disubstituted acid Ia generally in dissolved form. The salt can then be converted to the free acid Ia by acidifying the solution as described above. In general, the acid Ia is obtained as a solid and can be isolated by filtration and, if appropriate, dried. In this procedure, the 1,3-disubstituted pyrazolecarboxylic acid is obtained in high purity and with very good yield.

The acidic hydrolysis of the compound I can be carried out in analogy to known acidic ester hydrolyses, i.e. in the presence of catalytic or stoichiometric amounts of an acid and water (see, for example, J. March, Advanced Organic Chemistry, 2nd Ed., 334-338, McGraw-Hill, 1977 and literature cited there). Frequently, the reaction will be performed in a mixture of water and aprotic organic solvent, for example an ether as specified above. Examples of acids are hydrohalic acids, sulfuric acid, organic sulfonic acids such as p-toluenesulfonic acid, methanesulfonic acid, phosphoric acid and acidic anion exchangers, and the like.

Suitable hydrolysis catalysts are also alkali metal iodides such as lithium iodide, trimethyliodosilane or mixtures of trimethylchlorosilane with alkali metal iodides such as lithium, sodium or potassium iodide.

The acid Ia is then isolated by customary separation processes, for example precipitation by adjusting the pH or extraction.

When the $R^8$ radical is hydrogen, the conversion of the compound I to the carboxylic acid Ia typically comprises a bromination or chlorination step to obtain a 1,3-disubstituted 4-halopyrazole compound of the formula Ib

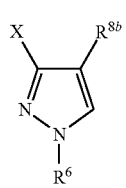

(Ib)

in which X and $R^6$ are each as defined above and $R^{8b}$ is chlorine or especially bromine.

The compound Ib can then be converted in a customary manner, for example via its Grignard compound, followed by a reaction with $CO_2$, if appropriate with transition metal catalysis, to the corresponding pyrazolecarboxylic acid of the formula Ia.

Accordingly, a further preferred embodiment of the invention relates to a process comprising the following steps:
a) the provision of a compound of the formula I in which $R^8$ is H by the process according to the invention as described,
b.1) halogenation of the compound I where $R^8$=H to obtain the compound Ib, and
b.2) conversion of the halogen compound Ib to the pyrazolecarboxylic acid of the formula Ia.

The halogenation of the pyrazole compound I where $R^8$=H can typically be carried out by reaction with suitable chlorinating or brominating agents, such as N-chloro-succinimide (NCS), sulfuryl chloride, $Cl_2$, $Br_2$, N-bromosuccinimide (NBS) or 1,3-dibromo-5,5-dimethylhydantoin (DDH) or a system consisting of $HBr/H_2O_2$.

Preferably, a bromination of the compounds of the formula I where R=H will be performed. The preferred brominating agent is elemental bromine ($Br_2$). In that case, preference is given to performing the bromination in an inert solvent, for example in an halogenated hydrocarbon such as dichloromethane. In this case, the reaction temperature is preferably in the range from −5 to 50° C. and especially room temperature. Further reaction conditions which are likewise appropriate to the aim are known to those skilled in the art. The bromination of compounds of the formula I where R=H can likewise preferably be carried out with N-bromosuccinimide (NBS) or 1,3-dibromo-5,5-dimethylhydantoin (DDH), and especially with NBS. Suitable solvents for this purpose are especially polar solvents, such as dimethylformamide, N-methyl-pyrrolidinone, 1,3-dimethyl-2-imidazolidinone, dimethylacetamide, dimethylethyleneurea, dimethylpropyleneurea (DMPU) or tetramethylurea, or mixtures of these solvents. The reaction temperature is typically within a range from −10 to 50° C.

The subsequent conversion of the halogenated pyrazole compound Ib to the pyrazolecarboxylic acid Ia can be effected by standard methods of organic chemistry. For example, the pyrazole compound Ib can be converted by reaction with magnesium or an organic magnesium compound to its Grignard compound which is then reacted with $CO_2$ to give the carboxylic acid Ia. Such methods are known to those skilled in the art, for example from J. March, Advanced Organic Chemistry, 3rd ed. J. Wiley and Sons, New York 1985, p. 826 ff. and the literature cited there.

The pyrazole compounds of the formula I, especially the pyrazolecarboxylic acids of the formula Ia, but also the compounds of the formula Ib, are valuable intermediates in the preparation of active ingredients which have a 1,3-disubstituted pyrazole radical, especially in the preparation of active fungicidal ingredients of the formula V described below:

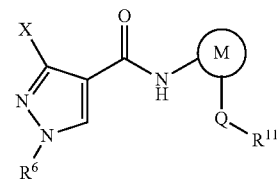

(V)

in which X and $R^6$ are each as defined for compound of the formula I,
M is thienyl or phenyl which may bear a halogen substituent;
Q is a direct bond, cyclopropylene, a fused bicyclo[2.2.1] heptane or bicyclo[2.2.1]heptene ring;
$R^{11}$ is hydrogen, halogen, $C_1$-$C_8$-alkyl, $C_1$-$C_4$-haloalkoxy, optionally substituted $C_2$-$C_6$-alkynyl, a mono- to trisubstituted phenyl,
    where the substituents are each independently selected from halogen and trifluoromethylthio,
    or optionally substituted cyclopropyl.

Accordingly, the present invention also relates to a process for preparing a compound of the formula V, comprising the following steps:
a) providing a pyrazole compound of the formula I by the process according to the invention
b) converting the compound I to a 1,3-disubstituted pyrazolecarboxylic acid of the formula Ia,

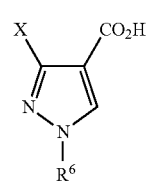

(Ia)

in which X and $R^6$ are each as defined above;
c) if appropriate converting the compound Ia to its acid halide, and
d) reacting the compound of the formula Ia or its acid halide with an amine compound of the formula IV,

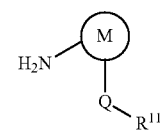

(IV)

in which M, Q and $R^{11}$ are each as defined for formula V.

Suitable methods for preparing carboxylic acids and by reaction of carboxylic acids or carbonyl halides with aromatic amines are known to those skilled in the art, for example from the prior art cited at the outset (see U.S. Pat. No. 5,498,624, EP 545099 A1, DE 19531813 A1, EP 589301 A1, DE 19840322 A1, WO 92/12970, WO 03/066610, WO 2006/024389, WO 2007/003603, WO 2007/006806) and from J. March, Advanced Organic Chemistry, 3rd ed. J. Wiley and Sons, New York 1985, p. 370-386 and literature cited there, and also Organikum, 21st edition, Wiley-VCH, Weinheim 2001, p. 481-484 and literature cited there, and can be applied to the inventive preparation of the compounds V by reacting the pyrazolecarboxylic acid Ia or acid halide thereof with the aniline compound IV in an analogous manner.

Frequently, the procedure will be first to convert the pyrazolecarboxylic acid of the formula Ia to its acid halide, for example its acid chloride, and then to react the acid halide with the amine compound of the formula IV. The pyrazolecarboxylic acid can be converted to its acid chloride in analogy to standard processes of organic chemistry, for example by reaction with thionyl chloride. The subsequent reaction of the acid halide with the amine compound IV is effected typically in the presence of an auxiliary base, for example a tertiary amine. Alternatively, the pyrazolecarboxylic acid of the formula Ia can also be reacted directly with the amine compound IV, preferably in the presence of a dehydrating agent such as 1,1'-carbonyldiimidazole, bis(2-oxo-3-oxazolidinyl)phosphoryl chloride, N,N'-dicyclohexylcarbodiimide or N-(3-dimethylamino-propyl)-N'-ethylcarbodiimide in the presence of an auxiliary base, for example a tertiary amine, to give the compound V, as described, for example, in prior patent application Wo 2008/077907, whose disclosure is hereby explicitly incorporated by reference.

The present invention also relates to a process for preparing a compound of the formula V, comprising the following steps:
a') providing a pyrazole compound of the formula I in which $R^8$ is H by a process according to the invention,
b') reacting the compound of the formula I in which $R^8$ is H to a chlorinating or brominating agent to obtain a pyrazole compound of the formula Ib,
c') the reaction of a compound of the formula Ib with carbon monoxide and with an amine compound of the formula IV in the presence of a palladium catalyst.

The reaction of the compound Ib with carbon monoxide and the compound IV in the presence of a palladium catalyst is described in prior application EP 07109463.5, whose disclosure is hereby incorporated by reference.

To this end, in step c', the compounds of the formulae Ib and IV are preferably used in a molar Ib:IV ratio of from 0.5:1 to 2:1, preferably from 0.8:1 to 1.2:1. In particular, the compound of the formula IV is used in a slight excess based on the compound Ib, i.e. the molar Ib:IV ratio is <1, for example in the range from 0.5:1 to <1:1, especially in the range from 0.8:1 to 0.95:1.

Suitable palladium catalysts for the reaction of the compounds of the formula Ib with compounds of the formula IV are palladium compounds in which palladium has an oxidation state of 0 or 2.

Examples of palladium compounds which have an oxidation state of 0 are palladium(0)-ligand complexes such as tetrakis(triphenylphosphine)palladium(0), tetrakis(diphenylmethylphosphine)palladium(0) or bis-(DIPHOS)palladium(0), or metallic palladium which is optionally supported. Metallic palladium is preferably applied to a support, such as activated carbon, aluminum oxide, barium sulfate, barium carbonate or calcium carbonate. The reaction in the presence of metallic palladium is effected preferably in the presence of suitable complex ligands.

Examples of palladium compounds which have an oxidation state of 2 are palladium (II)-ligand complexes such as palladium (II) acetylacetonate or compounds of the formula $PdX_2L_2$ in which X is halogen and L is a monovalent ligand, especially a ligand of the formulae (A) or (B) shown below, and also palladium (II) salts, for example palladium acetate or palladium chloride, preferably palladium chloride.

When palladium (II) salts are used, the reaction is effected preferably in the presence of suitable complex ligands, especially of the complex ligands of the formulae (A) and (B) shown below.

The palladium catalyst can be used in the form of a finished palladium catalyst or as a palladium compound which, under the reaction conditions, as a precatalyst, forms the catalytically active compounds together with suitable ligands.

Suitable complex ligands for the inventive reaction of compounds of the formula Ib with compounds of the formula IV are, for example, mono- or bidentate phosphines of the formulae (A) and (B) shown below

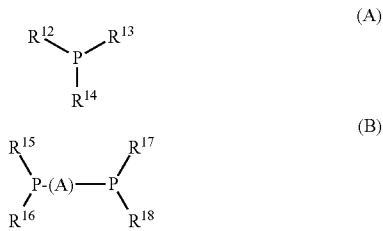

in which $R^{12}$ to $R^{19}$ are each independently $C_1$-$C_6$-alkyl, $C_5$-$C_8$-cycloalkyl, adamantyl, aryl-$C_1$-$C_2$-alkyl, or preferably ferrocenyl or aryl which may optionally be substituted by $C_1$-$C_4$-alkyl or $C_1$-$C_4$-alkoxy, and A is a linear, bivalent hydrocarbon group, preferably having from 2 to 5 carbon atoms, which is unsubstituted or optionally substituted, where the bivalent hydrocarbon group may be part of a mono- or bicyclic ring which is in turn unsubstituted or may have further substituents.

A in the compounds of the formula (A) and (B) is especially $C_2$-$C_4$-alkylene, $C_0$-$C_1$-alkyleneferrocenyl, 1,1'-biphenyl-2,2'-diyl or 1,1'-binaphthyl-2,2'-diyl, where the latter four groups may optionally be substituted by $C_1$-$C_4$-alkyl or $C_1$-$C_4$-alkoxy, and where $C_1$-$C_4$-alkylene may additionally have one or more substituents selected from $C_3$-$C_7$-cycloalkyl, aryl or benzyl. In this connection, aryl represents naphthyl or optionally substituted phenyl. Aryl preferably represents phenyl or toluol, more preferably phenyl.

$C_0$-$C_1$-alkyleneferrocenyl represents especially ferrocendiyl, where one of the two phosphorus atoms is bonded to each cyclopentadiene of the ferrocene, or methyleneferrocenyl, where one of the phosphorus atoms is bonded to the cyclopentadiene via the methylene group, the second phosphorus atom is bonded to the same cyclopentadiene and the methylene group may optionally have one or two further substituents selected from $C_1$-$C_4$-alkyl.

Preference is given to using, as complex ligands in the process according to the invention for preparing compounds of the formula Ib with compounds of the formula IV, bidentate phosphines such as 1,3-bis(diphenylphosphino)propane (DPPP), 1,3-bis(diphenylphosphino)ethane, 1,3-bis(dicyclohexylphosphino)propane (DCPP), ferrocenyl-containing phosphines of the JosiPhos type, 1,1'-bis(diphenyl-phosphino)ferrocene (DPPF) or 2,2-dimethyl-1,3-bis(diphenylphosphino)propane and more preferably 2,2-dimethyl-1,3-bis(diphenylphosphino)propane.

The palladium catalyst is used in the process according to the invention preferably in an amount of from 0.01 to 5 mol %, more preferably from 0.1 to 1 mol %, based on the amount of the pyrazole of the formula Ib used.

In a preferred embodiment, the process according to the invention for reacting compounds of the formula Ib with compounds of the formula IV is effected in the presence of an auxiliary base.

Suitable auxiliary bases are, for example, basic alkali metal salts and tertiary amines. Examples of basic alkali metal salts are potassium phosphate, sodium phosphate, potassium carbonate, sodium carbonate, potassium acetate or sodium acetate. The alkali metal should preferably be essentially anhydrous. Particular preference is given to using dry potassium carbonate or potassium phosphate. In this embodiment, alkali metal salts are used preferably in an amount of at least 1 molar equivalent, more preferably from 1 to 4 and especially about 2 molar equivalents, based on the amount of the pyrazole compound of the formula Ib used. Suitable tertiary amines are, for example, tri($C_1$-$C_6$-alkyl)amine such as trimethylamine, triethylamine or diisopropylethylamine, N-methylpiperidine, pyridine, substituted pyridines such as 2,4,6-trimethylpyridine (collidine), 2,6-dimethylpyridine (lutidine), 2-methylpyridine, α-picoline), 3-methylpyridine (β-picoline), 4-methylpyridine (γ-picoline) and 4-dimethylaminopyridine, and also bicyclic amines such as 1,4-diazabicyclo[2.2.2]octane, 1,8-diazabicyclo[5.4.0]undec-7-ene or 1,5-diazabicyclo[4.3.0]non-5-ene. Particular preference is given to using triethylamine, pyridine or 1,8-diazabicyclo[5.4.0]undec-7-ene. Tertiary amines can be used in an amount of from 0.1 to 4 molar equivalents based on the amount of the pyrazole compound of the formula Ib used.

In a preferred embodiment of the process according to the invention, a compound of the formula Ib is reacted with a compound of the formula IV in the presence of at least one tertiary amine and of at least one alkali metal salt.

In this embodiment, the alkali metal salt is used preferably in an amount of from 1 to 4 and especially of about 2 molar equivalents based on the amount of the pyrazole compound of the formula Ib used. In this embodiment, the tertiary amine is used preferably in an amount of from 0.1 to 4 molar equivalents, preferably from 0.2 to 0.7 molar equivalent, based on the amount of the pyrazole compound of the formula Ib used.

In this embodiment, the auxiliary base is used preferably in a total amount of from 2 to 5 molar equivalents, based on the amount of the pyrazole compound of the formula Ib used.

The compound of the formula Ib is reacted with a compound of the formula IV preferably in an organic solvent. Suitable solvents for the reaction of compounds of the formula Ib with compounds of the formula IV are polar solvents, for example amides such as dimethylformamide, dimethylacetamide, or N-methylpyrrolidone, ureas such as 1,3-dimethyl-2-imidazolidinone (DMEU) or 1,4-dimethylhexahydro-2-pyrimidinone (DMPU), ethers such as tetrahydrofuran (THF) and 1,4-dioxane, sulfolane, dimethylsulfoxide (DMSO) or nitriles such as acetonitrile or propionitrile, and mixtures of these solvents. Preference is given to using nitriles, especially acetonitrile. The solvent used is preferably essentially anhydrous, i.e. the solvent has a water content of less than 1000 ppm and especially not more than 100 ppm.

The reaction of compounds of the formula Ib with compounds of the formula IV in the process according to the invention is preferably carried out at a temperature of from 100 to 150° C., more preferably at a temperature of from 110 to 130° C.

The partial CO pressure in the reaction of compounds of the formula Ib with compounds of the formula IV is preferably within a range from 0.9 to 100 bar, more preferably within a range from 2 to 20 bar and especially within a range from 5 to 10 bar.

The reaction mixtures obtained in the reaction of compounds of the formula Ib are generally worked up under aqueous conditions, i.e. the resulting reaction mixture is contacted with water or an aqueous solution. After the aqueous reaction mixtures thus obtained have been acidified, the compounds of the formula IV can generally be isolated by extraction with an organic solvent and subsequent removal of the organic solvent. In some cases, it may be advantageous, especially in the case of use of water-miscible solvents for the reaction, to remove the solvent at least partly before the extraction, for example by distillation.

Examples of compounds of the formula V which can be prepared by processes described here are:

N-(2-bicyclopropyl-2-yl-phenyl)-3-difluoromethyl-1-methylpyrazol-4-ylcarboxamide (Sedoxane), N-(3',4',5'-trifluorobiphenyl-2-yl)-1,3-dimethylpyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-(chlorodifluoromethyl)-1-methylpyrazol-4-yl-carboxamide, N-(3',4',5'-trifluorobiphenyl-2-yl)-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-yl-carboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-(chlorodifluoromethyl)-1-methylpyrazol4-yl-carboxamide, N-(2',4',5'-trifluorobiphenyl-2-yl)-1-methyl-3-trifluoromethylpyrazol4-ylcarboxamide, N-(3',4'-dichloro-3-fluorobiphenyl-2-yl)-1-methyl-3-trifluoromethyl-1H-pyrazol-4-yl-carboxamide, N-(3',4'-dichloro-3-fluorobiphenyl-2-yl)-1-methyl-3-difluoromethyl-1H-pyrazol-4-yl-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-3-difluoromethyl-1H-pyrazol-4-yl-carboxamide, N-(3'-chloro-4'-fluoro-3-fluorobiphenyl-2-yl)-1-methyl-3-difluoromethyl-1H-pyrazol-4-yl-carboxamide, N-(3',4'-dichloro-4-fluorobiphenyl-2-yl)-1-methyl-3-trifluoromethyl-1H-pyrazol-4-yl-carboxamide, N-(3',4'-difluoro-4-fluorobiphenyl-2-yl)-1-methyl-3-trifluoromethyl-1H-pyrazol-4-yl-carboxamide, N-(3',4'-dichloro-4-fluorobiphenyl-2-yl)-1-methyl-3-difluoromethyl-1H-pyrazol-4-yl-carboxamide, N-(3',4'-difluoro-4-fluorobiphenyl-2-yl)-1-methyl-3-difluoromethyl-1H-pyrazol-4-yl-carboxamide, N-(3'-chloro-4'-fluoro-4-fluorobiphenyl-2-yl)-1-methyl-3-difluoromethyl-1H-pyrazol-4-yl-carboxamide, N-(3',4'-dichloro-5-fluorobiphenyl-2-yl)-1-methyl-3-trifluoromethyl-1H-pyrazol-4-yl-carboxamide (Bixafen), N-(3',4'-difluoro-5-fluorobiphenyl-2-yl)-1-methyl-3-trifluoromethyl-1H-pyrazol-4-yl-carboxamide, N-(3',4'-dichloro-5-fluorobiphenyl-2-yl)-1-methyl-3-difluoromethyl-1H-pyrazol-4-yl-carboxamide, N-(3',4'-difluoro-5-fluorobiphenyl-2-yl)-1-methyl-3-difluoromethyl-1H-pyrazol-4-yl-carboxamide, N-(3',4'-dichloro-5-fluorobiphenyl-2-yl)-1,3-dimethyl-1H-pyrazol-4-ylcarboxamide, N-(3'-chloro-4'-fluoro-5-fluorobiphenyl-2-yl)-1-methyl-3-difluoromethyl-1H-pyrazol-4-yl-carboxamide, N-(4'-fluoro-4-fluorobiphenyl-2-yl)-1-methyl-3-trifluoromethyl-1H-pyrazol-4-yl-carboxamide,
N-(4'-fluoro-5-fluorobiphenyl-2-yl)-1-methyl-3-trifluoromethyl-1H-pyrazol-4-yl-carboxamide,
N-(4'-chloro-5-fluorobiphenyl-2-yl)-1-methyl-3-trifluoromethyl-1H-pyrazol-4-yl-carboxamide,
N-(4'-methyl-5-fluorobiphenyl-2-yl)-1-methyl-3-trifluoromethyl-1H-pyrazol-4-yl-carboxamide,
N-(4'-fluoro-5-fluorobiphenyl-2-yl)-1,3-dimethyl-1H-pyrazol-4-ylcarboxamide,
N-(4'-chloro-5-fluorobiphenyl-2-yl)-1,3-dimethyl-1H-pyrazol-4-ylcarboxamide,
N-(4'-methyl-5-fluorobiphenyl-2-yl)-1,3-dimethyl-1H-pyrazol-4-ylcarboxamide,
N-(4'-fluoro-6-fluorobiphenyl-2-yl)-1-methyl-3-trifluoromethyl-1H-pyrazol-4-yl-carboxamide,
N-[2-(1,1,2,3,3,3-hexafluoropropoxy)-phenyl]-3-difluoromethyl-1-methyl-1H-pyrazol-4-ylcarboxamide,
N-[4'-(trifluoromethylthio)biphenyl-2-yl]-3-difluoromethyl-1-methyl-1H-pyrazol-4-ylcarboxamide,
N-[4'-(trifluoromethylthio)biphenyl-2-yl]-1-methyl-3-trifluoromethyl-1-methyl-1H-pyrazol-4-ylcarboxamide,
3-(difluoromethyl)-1-methyl-N-[1,2,3,4-tetrahydro-9-(1-methylethyl)-1,4-methanonaphthalen-5-yl]-1H-pyrazol-4-ylcarboxamide, (Isopyrazam)
N-(3'-chloro-5-fluorobiphenyl-2-yl)-3-(difluoromethyl)-1-methylpyrazol-4-ylcarboxamide,
N-(4'-chloro-5-fluorobiphenyl-2-yl)-3-(difluoromethyl)-1-methylpyrazol-4-ylcarboxamide,
N-(4'-chlorobiphenyl-2-yl)-3-(difluoromethyl)-1-methylpyrazol-4-ylcarboxamide,
N-(4'-bromobiphenyl-2-yl)-3-(difluoromethyl)-1-methylpyrazol-4-ylcarboxamide,
N-(4'-iodobiphenyl-2-yl)-3-(difluoromethyl)-1-methylpyrazol-4-ylcarboxamide,
N-(3',5'-difluorobiphenyl-2-yl)-3-(difluoromethyl)-1-methylpyrazol-4-ylcarboxamide,
N-(2-chloro-4-fluorophenyl)-3-(difluoromethyl)-1-methylpyrazol-4-ylcarboxamide,
N-(2-bromo-4-fluorophenyl)-3-(difluoromethyl)-1-methylpyrazol-4-ylcarboxamide,
N-(2-iodo-4-fluorophenyl)-3-(difluoromethyl)-1-methylpyrazol-4-ylcarboxamide and
N-[2-(1,3-dimethylbutyl)phenyl]-1,3-dimethyl-5-fluoro-1H-pyrazol-4-ylcarboxamide (Penfluen);
N-[2-(1,3-dimethylbutyl)-3-thienyl]-1-methyl-3-(trifluoromethyl)-1H-pyrazole-4-carboxamide (Pentiopyrate).

The examples which follow serve to further illustrate the invention.

PREPARATION EXAMPLE 1

Ethyl 3-difluoromethyl-1-methyl-1H-pyrazole-4-carboxylate

The aminal (200 mg, 0.56 mmol) was suspended in toluene (1.3 mL). Ethyl α-ethoxymethylene-4,4-difluoro-3-oxobutyrate (249 mg, 1.12 mmol) was added followed by methanesulfonic acid (11 mg, 0.11 mmol). The solution was stirred at 50° C. overnight; then, all volatiles were removed under reduced pressure and the residue was purified by flash column chromatography (SiO$_2$, hexanes/EtOAc) to give ethyl 3-difluoromethyl-1-methyl-1H-pyrazole-4-carboxylate as a colorless solid (176 mg, 0.86 mmol, 77% yield).

$^1$H NMR (500 MHz, DMSO-d$_6$): δ (ppm)=8.41 (s, 1H); 7.20 (t, J=54 Hz, 1H); 4.25 (q, J=7.0 Hz, 2H); 3.94 (s, 3H); 1.29 (t, J=7.0 Hz, 3H).

$^{13}$C NMR (125 MHz, DMSO-d$_6$): δ (ppm)=161.4; 145.1 (t=24 Hz); 136.3; 112.0 (t, J=3 Hz); 109.7 (t=234 Hz); 60.3; 39.3; 14.1.

$^{19}$F NMR (470 MHz, DMSO-d$_6$): δ (ppm)=126.2 (d, J=54 Hz).

mp=64° C.

PREPARATION EXAMPLE 2

Ethyl 3-difluoromethyl-1-methyl-1H-pyrazole-4-carboxylate

In a sealed tube, the aminal (200 mg, 0.56 mmol) was suspended in toluene (1.3 mL). Ethyl α-ethoxymethylene-4,4-difluoro-3-oxobutyrate (249 mg, 1.12 mmol) was added followed by toluenesulfonic acid monohydrate (21 mg, 0.11 mmol). The solution was stirred at 22° C. for 2 h. Then, a sample was taken and the conversion was determined by GC analysis (calibrated with dodecane as internal standard). According to the GC, 71% conversion to ethyl 3-difluoromethyl-1-methyl-1H-pyrazole-4-carboxylate were observed.

a) In a similar manner, the reaction was conducted in the presence of 1 equivalent (10 mg) of water. According to the GC (calibrated with dodecane as internal standard), 83% conversion to ethyl 3-difluoromethyl-1-methyl-1H-pyrazole-4-carboxylate were observed.

b) In a similar manner, the reaction was conducted in the presence of 2 equivalents (20 mg) of water. According to the GC (calibrated with dodecane as internal standard), 83% conversion to ethyl 3-difluoromethyl-1-methyl-1H-pyrazole-4-carboxylate were observed.

c) In a similar manner, the reaction was conducted in the presence of 5 equivalents (51 mg) of water. According to the GC (calibrated with dodecane as internal standard), 84% conversion to ethyl 3-difluoromethyl-1-methyl-1H-pyrazole-4-carboxylate were observed.

d) In a similar manner, the reaction was conducted in the presence of 10 equivalents (101 mg) of water. According to the GC (calibrated with dodecane as internal standard), 80% conversion to ethyl 3-difluoromethyl-1-methyl-1H-pyrazole-4-carboxylate were observed.

PREPARATION EXAMPLE 3

3-Difluoromethyl-1-methyl-1H-pyrazole-4 carboxylic acid without isolation/purification of the intermediates (three-step, one-pot sequence from azinium salt)

The azinium salt (10.0 g, 29.9 mmol) was suspended in 50 mL of toluene. A solution of NaOH (1.44 g, 36.0 mmol) in 50 mL of water was added and the biphasic mixture was heated to 60° C. for 3 h. The mixture was then cooled to rt, the phases split and the aqueous phase extracted with 20 mL of toluene. The combined org. phases were used in the next step without further purification. To the solution of the aminal in toluene were added ethyl α-ethoxymethylene-4,4-difluoro-3-oxobutyrate (6.64 g, 29.9 mmol) and p-TsOH monohydrate (0.57 g, 3.0 g). The solution was stirred overnight at rt, then heated to 60° C. for one hour. The solution was then cooled to rt and extracted with 30 mL sat. NaHCO$_3$ solution. The org. phase was used in the next step without further purification. To the org. phase was added 10% KOH solution (24.1 g). The biphasic mixture was heated to 60° C. and the disappearance of the ester monitored by GC. When the ester had completely vanished, the solution was cooled to rt. The phases were then split and the aqueous phase was heated to 55° C. Then, 30%

H₂SO₄ solution (16 g) were added and stirring continued for 60 min. The solution was then cooled to 5° C. and the precipitated product removed by filtration. The precipitate was washed with cold water and dried under reduced pressure overnight (p<20 mbar, 50° C.). The product was obtained as a yellow powder (2.87 g, 16.3 mmol, 55% yield based on the azinium salt).

$^1$H NMR (500 MHz, DMSO-d₆): δ (ppm)=8.33 (s, 1H); 7.22 (t, J=54 Hz, 1H); 3.93 (s, 3H).

$^{13}$C NMR (125 MHz, DMSO-d₆): δ (ppm)=163.0; 145.1 (t, J=24 Hz); 136.1; 113.0 (t, J=3 Hz); 109.6 (t, J=234 Hz); 39.2.

$^{19}$F NMR (470 MHz, DMSO-d₆): δ (ppm)=−126.0 (d, J=54 Hz).

mp=205° C.

Purity (cal. HPLC): 97.1% (0.4% iso-DFP acid)

PREPARATION EXAMPLE 4

3-difluoromethyl-1-methyl-1H-pyrazole-4 carboxylic acid without isolation/purification of the intermediates (four-step, one-pot sequence from azine)

Dibenzaldazine (25.0 g, 120 mmol) was suspended in 100 mL of toluene. The suspension was heated to 50° C. and all azine went into solution. Me₂SO₄ (22.7 g, 180 mmol) was added, the solution was heated to 85° C. and stirring was continued at that temperature overnight (16 h). During that time, the product separated as a yellow precipitate. The mixture was cooled to 40° C. and NaOH (9.6 g, 240 mmol) in 200 mL of water was added. The biphasic mixture was heated to 60° C. and stirred for 3 h. The solution was cooled to rt, the phases were separated and the aqueous phase was washed with toluene (60 mL). The organic phases were combined and used in the next step. To the afore prepared solution was added Ethyl α-ethoxymethylene-4,4-difluoro-3-oxobutyrate (24.0 g, 108 mmol), p-TsOH (1.03 g, 5.4 mmol) and water (1.95 g, 108 mmol). The mixture was heated to 60° C. for 3 h (at that time GC showed full conversion). After cooling to rt, the org. phase was extracted with sat. NaHCO₃ solution (60 mL). To the organic phase was then added 10% KOH (121 g) and the biphasic mixture was heated to 60° C. for 3 h and stirred at rt overnight (on the next day GC showed complete saponification of the ester). The phases were split and the org. phase separated with 60 mL of water. The combined aqueous phases were warmed to 55° C. and 30% H₂SO₄ (71.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (12.5 g, 71.0 mmol, 59% yield based on the azine).

Purity (cal. HPLC): 97.4% (no iso-DFP acid)

PREPARATION EXAMPLE 5

3-difluoromethyl-1-methyl-1H-pyrazole-4 carboxylic acid without isolation/purification of the intermediates (five-step, one-pot sequence from hydrazine)

Benzaldehyde (24.0 g, 226 mmol) was dissolved in 240 mL of toluene. Hydrazine hydrate (5.0 g, 100 mmol) was added dropwise; the solution was heated to 90° C. and stirring was continued for 3 h. Then, a Dean-Stark apparatus was attached and water was removed by azeotropic distillation. The solution was then cooled to 70° C. and Me₂SO₄ (18.9 g, 150 mmol) was added. The solution was heated to 85° C. overnight. During that time a yellow precipitate formed. The mixture was cooled to 40° C. and 100 mL of toluene were added, followed by a solution of NaOH (8.0 g, 200 mmol) in 170 g of water. Die biphasic mixture was heated to 60° C. and stirred for further 3 h at that temperature. The solution was cooled to rt, the phases were separated and the aqueous phase was washed with toluene (50 mL). The organic phases were combined and used in the next step. To the afore prepared solution were added Ethyl α-ethoxymethylene-4,4-difluoro-3-oxobutyrate (20.0 g, 90.0 mmol), p-TsOH (0.9 g, 4.5 mmol) and water (1.62 g, 90.0 mmol). The mixture was heated to 60° C. for 3 h (at that time GC showed full conversion). After cooling to rt, the org. phase was extracted with sat. NaHCO₃ solution (60 mL). To the organic phase was then added 10% KOH (101 g) and the biphasic mixture was heated to 60° C. for 3 h and stirred at rt overnight (on the next day GC showed complete saponification of the ester). The phases were split and the org. phase separated with 50 mL of water. The combined aqueous phases were warmed to 55° C. and 30% H₂SO₄ (59.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (11.2 g, 63.5 mmol, 64% yield based on hydrazine).

Purity (cal. HPLC): 96.7% (no iso-DFP acid)

PREPARATION EXAMPLE 6

Ethyl 3-difluoromethyl-1-methyl-1H-pyrazole-4-carboxylate

The aminal (1.00 g, 2.81 mmol) was dissolved in 7 mL of toluene. Then, ethyl α-ethoxymethylene-4,4-difluoro-3-oxobutyrate (1.25 g, 5.62 mmol) and p-TsOH (107 mg, 0.56 mmol) were added, followed by water (101 mg, 5.62 mg). The mixture was stirred at rt for 90 min, then GC control showed >97% conversion to the pyrazole. The reaction mixture was extracted with water (2×1 mL); then, the organic phase was concentrated under reduced pressure and the residue purified by column chromatography (SiO₂, cyclohexane/EtOAc 100:0→70:30) to give the product (840 mg, 4.12 mmol, 73% yield) as a colorless solid.

$^1$H NMR (500 MHz, DMSO-d₆): δ (ppm)=8.41 (s, 1H); 7.20 (t, J=54 Hz, 1H); 4.25 (q, J=7.0 Hz, 2H); 3.94 (s, 3H); 1.29 (t, J=7.0 Hz, 3H).

$^{13}$C NMR (125 MHz, DMSO-d₆): δ (ppm)=161.4; 145.1 (t=24 Hz); 136.3; 112.0 (t, J=3 Hz); 109.7 (t=234 Hz); 60.3; 39.3; 14.1.

$^{19}$F NMR (470 MHz, DMSO-d₆): δ (ppm)=−126.2 (d, J=54 Hz).

mp=64° C.

PREPARATION EXAMPLE 7a

3-Difluoromethyl-1-methyl-1H-pyrazole-4-carboxylic acid from N,N'-dibenzylidene-N-methylhydrazinium methylsulfate without isolation/purification of any intermediates (three-step, one-pot sequence from azinium salt)

The azinium salt (10.0 g, 29.9 mmol) was suspended in 50 mL of toluene. A solution of NaOH (1.44 g, 36.0 mmol) in 50 mL of water was added and the biphasic mixture was heated to 60° C. for 3 h. The mixture was then cooled to rt, the phases split and the aqueous phase extracted with 20 mL of toluene.

The combined org. phases were used in the next step without further purification. To the solution of the aminal in toluene were added ethyl α-ethoxymethylene-4,4-difluoro-3-oxobutyrate (6.64 g, 29.9 mmol) and p-TsOH monohydrate (0.57 g, 3.0 mmol). The solution was stirred overnight at rt, then heated to 60° C. for one hour. The solution was then cooled to it and extracted with 30 mL sat. NaHCO$_3$ solution. The org. phase was used in the next step without further purification. To the org. phase was added 10% KOH solution (24.1 g). The biphasic mixture was heated to 60° C. and the disappearance of the ester monitored by GC. When the ester had completely vanished, the solution was cooled to rt. The phases were then split and the aqueous phase was heated to 55° C. Then, 30% H$_2$SO$_4$ solution (16 g) were added and stirring continued for 60 min. The solution was then cooled to 5° C. and the precipitated product removed by filtration. The precipitate was washed with cold water and dried under reduced pressure overnight (p<20 mbar, 50° C.). The product was obtained as a yellow powder (2.87 g, 16.3 mmol, 55% yield based on the azinium salt).

$^1$H NMR (500 MHz, DMSO-d$_6$): δ (ppm)=8.33 (s, 1H); 7.22 (t, J=54 Hz, 1H); 3.93 (s, 3H).

$^{13}$C NMR (125 MHz, DMSO-d$_6$): δ (ppm)=163.0; 145.1 (t, J=24 Hz); 136.1; 113.0 (t, J=3 Hz); 109.6 (t, J=234 Hz); 39.2.

$^{19}$F NMR (470 MHz, DMSO-d$_6$): δ (ppm)=–126.0 (d, J=54 Hz).

mp=205° C.

Purity (cal. HPLC): 97.1% (0.4% iso-DFP acid)

PREPARATION EXAMPLE 7b 3-difluoromethyl-1-methyl-1H-pyrazole-4-carboxylic acid from 2-furancarboxaldehyde without isolation/purification of any intermediates (three-step, one-pot sequence from azinium salt)

The azinium salt (5.0 g, 15.3 mmol) was suspended in 25 mL of toluene. A solution of NaOH (0.74 g, 18.4 mmol) in 25 mL of water was added and the biphasic mixture was stirred at rt for 6 h. The phases were split and the aqueous phase extracted with 20 mL of toluene. The combined org. phases were used in the next step without further purification. To the solution of the aminal in toluene were added ethyl α-ethoxymethylene-4,4-difluoro-3-oxobutyrate (5.4 g, 24.5 mmol) and p-TsOH monohydrate (0.23 g, 1.2 mmol). The solution was stirred overnight at rt, then heated to 50° C. for six hours. The solution was then cooled to rt and extracted with 30 mL sat. NaHCO$_3$ solution. The org. phase was used in the next step without further purification. To the org. phase was added 10% NaOH solution (61.2 g). The biphasic mixture was heated to 60° C. and the disappearance of the ester monitored by GC. When the ester had completely vanished, the solution was cooled to rt. The phases were then split and the aqueous phase was heated to 55° C. Then, 30% H$_2$SO$_4$ solution (16 g) were added and stirring continued for 60 min. The solution was then cooled to 5° C. and the precipitated product removed by filtration. The precipitate was washed with cold water and dried under reduced pressure overnight (p<20 mbar, 50° C.). The product was obtained as a yellow powder (0.63 g, 3.6 mmol, 24% yield based on the azinium salt).

Purity (cal. HPLC): 72.5%

PREPARATION EXAMPLE 7c

3-Difluoromethyl-1-ethyl-1H-pyrazole-4-carboxylic acid from N,N'-dibenzylidene-N-ethylhydrazinium ethylsulfate without isolation/purification of any intermediates (three-step, one-pot sequence from azinium salt)

The azinium salt (8.4 g, 20.0 mmol) was suspended in 40 mL of toluene and cooled to 3° C. A solution of NaOH (1.6 g, 40.0 mmol) in 38 mL of water was added and the biphasic mixture was warmed to rt for 1 h. The mixture was then cooled to rt, the phases split and the aqueous phase extracted with 20 mL of toluene. The combined org. phases were used in the next step without further purification. To the solution of the aminal in toluene were added ethyl α-ethoxymethylene-4,4-difluoro-3-oxobutyrate (4.4 g, 20.0 mmol) and p-TsOH monohydrate (0.19 g, 1.0 mmol). The solution was stirred 30 mint at rt, then heated to 60° C. for five hours. The solution was then cooled to it and extracted with 30 mL sat. NaHCO$_3$ solution. The org. phase was used in the next step without further purification. To the org. phase was added 10% KOH solution (22.4 g). The biphasic mixture was heated to 60° C. and the disappearance of the ester monitored by GC. When the ester had completely vanished, the solution was cooled to rt. The phases were then split and the aqueous phase was heated to 55° C. Then, 30% H$_2$SO$_4$ solution (16 g) were added and stirring continued for 60 min. The solution was then cooled to 5° C. and the precipitated product removed by filtration. The precipitate was washed with cold water and dried under reduced pressure overnight (p<20 mbar, 50° C.). The product was obtained as a tan powder (1.5 g, 7.9 mmol, 40% yield based on the azinium salt).

$^1$H NMR (500 MHz, CDCl$_3$): δ (ppm)=10.40 (s, 1H); 8.01 (s, 1H); 7.11 (t, J=67 Hz, 1H); 4.26 (q, J=9.0 Hz, 2H); 1.55 (t, J=9.0 Hz, 3H).

mp=152° C.

PREPARATION EXAMPLE 8a 3-difluoromethyl-1-methyl-1H-pyrazole-4-carboxylic acid from dibenzaldazine without isolation/purification of the intermediates (four-step, one-pot sequence from azine)

Dibenzaldazine (25.0 g, 120 mmol) was suspended in 100 mL of toluene. The suspension was heated to 50° C. and all azine went into solution. Me$_2$SO$_4$ (22.7 g, 180 mmol) was added, the solution was heated to 85° C. and stirring was continued at that temperature overnight (16 h). During that time, the product separated as a yellow precipitate. The mixture was cooled to 40° C. and NaOH (9.6 g, 240 mmol) in 200 mL of water was added. The biphasic mixture was heated to 60° C. and stirred for 3 h. The solution was cooled to rt, the phases were separated and the aqueous phase was washed with toluene (60 mL). The organic phases were combined and used in the next step. To the afore prepared solution was added ethyl α-ethoxymethylene-4,4-difluoro-3-oxobutyrate (24.0 g, 108 mmol), p-TsOH (1.03 g, 5.4 mmol) and water (1.95 g, 108 mmol). The mixture was heated to 60° C. for 3 h (at that time GC showed full conversion). After cooling to rt, the org. phase was extracted with sat. NaHCO$_3$ solution (60 mL). To the organic phase was then added 10% KOH (121 g) and the biphasic mixture was heated to 60° C. for 3 h and stirred at rt overnight (on the next day GC showed complete saponification of the ester). The phases were split and the org. phase separated with 60 mL of water. The combined aqueous phases were warmed to 55° C. and 30% $H_2SO_4$ (71.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (12.5 g, 71.0 mmol, 59% yield based on the azine).

Purity (cal. HPLC): 97.4% (no iso-DFP acid)

PREPARATION EXAMPLE 8b 3-difluoromethyl-1-methyl-1H-pyrazole-4-carboxylic acid from 4-anisaldehyde azine without isolation/purification of any intermediates (four-step, one-pot sequence from azine)

4-Anisaldehyde azine (32.2 g, 120 mmol) was suspended in 100 mL of toluene. The suspension was heated to 50° C. and $Me_2SO_4$ (22.7 g, 180 mmol) was added. The solution was heated to 85° C. and stirring was continued at that temperature overnight (16 h). During that time, the product separated as a yellow precipitate. The mixture was cooled to 40° C. and NaOH (9.6 g, 240 mmol) in 200 mL of water was added. The biphasic mixture was heated to 60° C. and stirred for 3 h. The solution was cooled to rt, the phases were separated and the aqueous phase was washed with toluene (60 mL). The organic phases were combined and used in the next step. To the afore prepared solution was added ethyl α-ethoxymethylene-4,4-difluoro-3-oxobutyrate (24.0 g, 108 mmol), p-TsOH (1.03 g, 5.4 mmol) and water (1.95 g, 108 mmol). The mixture was heated to 60° C. for 3 h (at that time GC showed full conversion). After cooling to rt, the org. phase was extracted with sat. $NaHCO_3$ solution (60 mL). To the organic phase was then added 10% KOH (121 g) and the biphasic mixture was heated to 60° C. for 3 h and stirred at it overnight (on the next day GC showed complete saponification of the ester). The phases were split and the org. phase separated with 60 mL of water. The combined aqueous phases were warmed to 55° C. and 30% $H_2SO_4$ (71.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (13.5 g, 76.4.0 mmol, 64% yield based on the azine).

Purity (cal. HPLC): 93.4% (no iso-DFP acid)

PREPARATION EXAMPLE 9a 3-difluoromethyl-1-methyl-1H-pyrazole-4-carboxylic acid from benzaldehyde without isolation/purification of any intermediates (five-step, one-pot sequence from hydrazine)

Benzaldehyde (24.0 g, 226 mmol) was dissolved in 240 mL of toluene. Hydrazine hydrate (5.0 g, 100 mmol) was added dropwise; the solution was heated to 90° C. and stirring was continued for 3 h. Then, a Dean-Stark apparatus was attached and water was removed by azeotropic distillation. The solution was then cooled to 70° C. and $Me_2SO_4$ (18.9 g, 150 mmol) was added. The solution was heated to 85° C. overnight. During that time a yellow precipitate formed. The mixture was cooled to 40° C. and 100 mL of toluene were added, followed by a solution of NaOH (8.0 g, 200 mmol) in 170 g of water. Die biphasic mixture was heated to 60° C. and stirred for further 3 h at that temperature. The solution was cooled to rt, the phases were separated and the aqueous phase was washed with toluene (50 mL). The organic phases were combined and used in the next step. To the afore prepared solution were added ethyl α-ethoxymethylene-4,4-difluoro-3-oxobutyrate (20.0 g, 90.0 mmol), p-TsOH (0.9 g, 4.5 mmol) and water (1.62 g, 90.0 mmol). The mixture was heated to 60° C. for 3 h (at that time GC showed full conversion). After cooling to rt, the org. phase was extracted with sat. $NaHCO_3$ solution (60 mL). To the organic phase was then added 10% KOH (101 g) and the biphasic mixture was heated to 60° C. for 3 h and stirred at rt overnight (on the next day GC showed complete saponification of the ester). The phases were split and the org. phase separated with 50 mL of water. The combined aqueous phases were warmed to 55° C. and 30% $H_2SO_4$ (59.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (11.2 g, 63.5 mmol, 64% yield based on hydrazine).

Purity (cal. HPLC): 96.7% (no iso-DFP acid)

PREPARATION EXAMPLE 9b 3-difluoromethyl-1-methyl-1H-pyrazole-4-carboxylic acid from 4-anisaldehyde without isolation/purification of any intermediates (five-step, one-pot sequence from hydrazine)

4-Anisaldehyde (40.8 g, 300 mmol) was dissolved in 240 g of toluene. Hydrazine hydrate (5.0 g, 100 mmol) was added dropwise; the solution was heated to 90° C. and stirring was continued for 4 h. Then, a Dean-Stark apparatus was attached and water and 90 g of toluene were removed by azeotropic distillation. The solution was then cooled to 75° C. and $Me_2SO_4$ (18.9 g, 150 mmol) was added. The solution was heated to 85° C. overnight. During that time an orange precipitate formed. The mixture was cooled to 40° C. and 100 mL of toluene were added, followed by a solution of NaOH (8.0 g, 200 mmol) in 170 g of water. Die biphasic mixture was heated to 60° C. and stirred for further 3 h at that temperature. The solution was cooled to rt, the phases were separated and the aqueous phase was washed with toluene (50 g). The organic phases were combined and used in the next step. To the afore prepared solution were added ethyl α-ethoxymethylene-4,4-difluoro-3-oxobutyrate (20.0 g, 90.0 mmol), p-TsOH (0.9 g, 4.5 mmol) and water (1.62 g, 90.0 mmol). The mixture was heated to 60° C. for 3 h (at that time GC showed full conversion). After cooling to rt, the org. phase was extracted with sat. $NaHCO_3$ solution (60 mL). To the organic phase was then added 10% KOH (101 g) and the biphasic mixture was heated to 60° C. for 3 h and stirred at rt overnight (on the next day GC showed complete saponification of the ester). The phases were split and the org. phase separated with 50 mL of water. The combined aqueous phases were warmed to 55° C. and 30% $H_2SO_4$ (59.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (8.0 g, 45.4 mmol, 45% yield based on hydrazine).

Purity (cal. HPLC): 93.4% (no iso-DFP acid)

PREPARATION EXAMPLE 9c 3-difluoromethyl-1-methyl-1H-pyrazole-4-carboxylic acid from 4-chlorobenzaldehyde without isolation/purification of any intermediates (five-step, one-pot sequence from hydrazine)

4-Chlorobenzaldehyde (30.9 g, 220 mmol) was dissolved in 240 g of toluene. Hydrazine hydrate (5.0 g, 100 mmol) was added dropwise; the solution was heated to 90° C. and stirring was continued for 3 h. Then, a Dean-Stark apparatus was attached and water and toluene (90 g) were removed by azeotropic distillation. The solution was then cooled to 75° C. and $Me_2SO_4$ (18.9 g, 150 mmol) was added. The solution was heated to 85° C. overnight. During that time a yellow precipitate formed. The mixture was cooled to 40° C. and 100 mL of toluene were added, followed by a solution of NaOH (8.0 g, 200 mmol) in 170 g of water. Die biphasic mixture was heated to 60° C. and stirred for further 3 h at that temperature. The solution was cooled to rt, the phases were separated and the aqueous phase was washed with toluene (50 g). The organic phases were combined and used in the next step. To the afore prepared solution were added ethyl α-ethoxymethylene-4,4-difluoro-3-oxobutyrate (20.0 g, 90.0 mmol), p-TsOH (0.9 g, 4.5 mmol) and water (1.62 g, 90.0 mmol). The mixture was heated to 60° C. for 3 h (at that time GC showed full conversion). After cooling to rt, the org. phase was extracted with sat. $NaHCO_3$ solution (60 mL). To the organic phase was then added 10% KOH (101 g) and the biphasic mixture was heated to 60° C. for 3 h and stirred at rt overnight (on the next day GC showed complete saponification of the ester). The phases were split and the org. phase separated with 50 mL of water. The combined aqueous phases were warmed to 55° C. and 30% $H_2SO_4$ (59.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (4.3 g, 24.2 mmol, 24% yield based on hydrazine).

Purity (cal. HPLC): 90.7% (0.6%

The invention claimed is:
1. A process for preparing a compound formula (I)

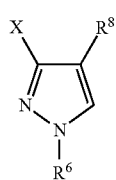

in which

X is hydrogen, branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein
  aryl or hetaryl are unsubstituted or optionally comprising one or more substituents independently of one another selected from the group consisting of $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile and carboxylic ester; or a $CX^1X^2X^3$ group, in which
  $X^1$, $X^2$ and $X^3$ are each independently hydrogen, fluorine or chlorine, where $X^1$ may also be $C_1$-$C_6$-alkyl or $C_1$-$C_4$-haloalkyl;

$R^6$ is branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein aryl or hetaryl are unsubstituted or optionally comprising one or more substituents independently of one another selected from the group consisting of halogen, hydroxo, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;

$R^8$ is hydrogen, methyl, hydroxymethylene, halogen, CHO, CN, $NO_2$ or a $CO_2R^{8a}$ group, in which
  $R^{8a}$ is $C_5$-$C_6$-cycloalkyl, optionally substituted phenyl or $C_1$-$C_6$-alkyl, which may optionally be substituted by $C_1$-$C_4$-alkoxy, phenyl or $C_3$-$C_6$-cycloalkyl;

comprising:
(i) reacting a compound of the formula (II) with a compound of the formula (III)

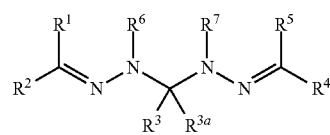

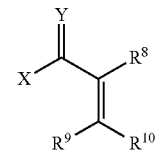

in which
$R^1$, $R^2$, $R^3$, $R^{3a}$, $R^4$, $R^5$ and $R^7$ are each independently hydrogen, branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein
  aryl or hetaryl are unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;

Y is oxygen, an $NR^{y1}$ group or an $[NR^{y2}R^{y3}]^+Z^-$ group, in which
  $R^{y1}$, $R^{y2}$ and $R^{y3}$ are each independently $C_1$-$C_8$-alkyl, $C_3$-$C_8$-cycloalkyl, optionally substituted phenyl or optionally substituted phenyl-$C_1$-$C_4$-alkyl, or $R^{y2}$ and $R^{y3}$ together with the nitrogen atom to which they are bonded form N-bonded, 5- to 8-membered, saturated, optionally substituted heterocycle which, as well as the nitrogen atom, may also comprise 1 or 2 further heteroatoms selected from the group consisting of N, O and S as ring atoms, and
  $Z^-$ is an anion, $R^9$ is halogen, $OR^{9a}$, $SR^{9a}$ or an $NR^{9b}R^{9c}$ group, in which
  $R^{9a}$, $R^{9b}$ and $R^{9c}$ are each independently $C_1$-$C_8$-alkyl, $C_3$-$C_8$-cycloalkyl, optionally substituted phenyl or optionally substituted phenyl-$C_1$-$C_4$-alkyl, or $R^{9b}$ and $R^{9c}$ together with the nitrogen atom to which they are bonded form an N-bonded 5- to 8-membered, saturated, optionally substituted heterocycle which, as well as the nitrogen atom, may also comprise 1 or 2 further heteroatoms selected from the group consisting of N, O and S as ring atoms; or a $CX^1X^2X^3$ group, in which
$X^1$, $X^2$ and $X^3$ are each independently hydrogen, fluorine or chlorine, where $X^1$ may also be $C_1$-$C_8$-alkyl or $C_1$-$C_4$-haloalkyl;

$R^{10}$ is hydrogen, halogen or $C_1$-$C_8$-alkyl;

(ii) treating the reaction product obtained with an acid, optionally in the presence of water.

2. The process according to claim 1, in which
Y is oxygen.

3. The process according to claim 1, in which
X is a $CX^1X^2X^3$ group in which
$X^1$ and $X^2$ are each fluorine and $X^3$ is hydrogen, fluorine or chlorine.

4. The process according to claim 1, in which
$R^8$ is a $COOR^{8a}$ group.

5. The process according to claim 1, in which
$R^6$ is $C_1$-$C_8$-alkyl or $C_3$-$C_8$-cycloalkyl.

6. The process according to claim 1, in which
$R^6$ is $C_1$-$C_3$-alkyl.

7. The process according to claim 1, in which
$R^6$ is methyl.

8. A process for preparing a pyrazolecarboxylic acid of the formula Ia

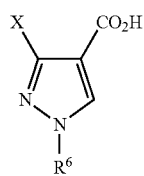

(Ia)

in which
X is hydrogen, branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein
aryl or hetaryl are unsubstituted or optionally comprising one or more substituents independently of one another selected from the group consisting of $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile and carboxylic ester; or
a $CX^1X^2X^3$ group, in which
$X^1$, $X^2$ and $X^3$ are each independently hydrogen, fluorine or chlorine, where $X^1$ may also be $C_1$-$C_6$-alkyl or $C_1$-$C_4$-haloalkyl;

$R^6$ is branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein aryl or hetaryl are unsubstituted or optionally comprising one or more substituents independently of one another selected from the group consisting of halogen, hydroxo, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;

comprising:

a) providing the compound of formula (I) as prepared by the process of claim 1;

b) converting the compound of formula (I) to the compound formula (Ia).

9. The process according to claim 8, in which
Y is oxygen.

10. The process according to claim 8, in which
X is a $CX^1X^2X^3$ group in which
$X^1$ and $X^2$ are each fluorine and $X^3$ is hydrogen, fluorine or chlorine.

11. The process according to claim 8, in which
$R^6$ is $C_1$-$C_8$-alkyl or $C_3$-$C_8$-cycloalkyl.

12. The process according to claim 8, in which
$R^6$ is $C_1$-$C_3$-alkyl.

13. The process according to claim 8, in which
$R^6$ is methyl.

14. A process for preparing a compound of the formula (V)

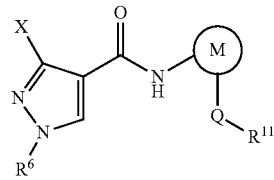

(V)

in which
X is hydrogen, branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein
aryl or hetaryl are unsubstituted or optionally comprising one or more substituents independently of one another selected from the group consisting of $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile and carboxylic ester; or
a $CX^1X^2X^3$ group, in which
$X^1$, $X^2$ and $X^3$ are each independently hydrogen, fluorine or chlorine, where $X^1$ may also be $C_1$-$C_6$-alkyl or $C_1$-$C_4$-haloalkyl;

$R^6$ is branched or unbranched $C_1$-$C_8$-alkyl, $C_2$-$C_8$-alkenyl or $C_3$-$C_8$-akynyl; $C_3$-$C_8$-cycloalkyl, aryl or hetaryl, wherein aryl or hetaryl are unsubstituted or optionally comprising one or more substituents independently of one another selected from the group consisting of halogen, hydroxo, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;

M is thienyl or phenyl which may bear a halogen substituent;

Q is a direct bond, cyclopropylene, a fused bicyclo[2.2.1]heptane or bicyclo[2.2.1]heptene ring;

$R^{11}$ is hydrogen, halogen, $C_1$-$C_8$-alkyl, $C_1$-$C_4$-haloalkoxy, optionally substituted $C_2$-$C_6$-alkynyl, a mono- to trisubstituted phenyl,
where the substituents are each independently selected from halogen and trifluoromethylthio,
or optionally substituted cyclopropyl;

comprising:
(i) providing the compound of formula (I) as prepared by the process of claim 1;
(ii) converting the compound (I) to the compound of formula (Ia)

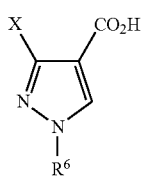

(Ia)

(iii) optionally converting the compound of formula (Ia) to its acid halide; and
(iv) reacting the compound of formula (Ia) or its acid halide with an amine compound of formula (IV),

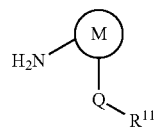

(IV)

or
(i') providing the compound of formula (I) as prepared by the process of claim 1;
(ii') reacting the compound of formula (I) in which $R^8$ is H with a chlorinating or brominating agent to obtain the compound of formula (Ib)

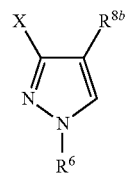

(Ib)

in which
$R^{8b}$ is chlorine or bromine;
(iii') reacting of a compound of the formula (Ib) with carbon monoxide and with an amine compound of the formula (IV) in the presence of a palladium catalyst.
15. The process according to claim 14, in which $R^6$ is C1-C8:alkyl or C3-C8-cycloalkyl.
16. The process according to claim 14, in which $R^6$ is C1-C3-alkyl.
17. The process according to claim 14, in which $R^6$ is methyl.
18. The process according to claim 14, in which Y is oxygen.
19. The process according to claim 14, in which X is a $CX^1X^2X^3$ group in which
$X^1$ and $X^2$ are each fluorine and $X^3$ is hydrogen, fluorine or chlorine.

* * * * *